United States Patent [19]

VandenBerg

[11] Patent Number: Plant 7,477

[45] Date of Patent: Mar. 19, 1991

[54] CHRYSANTHEMUM PLANT NAMED TIERNO

[75] Inventor: Cornelis P. VandenBerg, Salinas, Calif.

[73] Assignee: Yoder Brothers, Inc., Barberton, Ohio

[21] Appl. No.: 409,637

[22] Filed: Sep. 18, 1989

[51] Int. Cl.[5] ..... A01H 5/00

[52] U.S. Cl. ..... Plt./74

[58] Field of Search ..... Plt./74

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Tierno particularly characterized by its flat capitulum form; daisy capitulum type; red-purple ray floret color; diameter across face of capitulum of up to 9 cm at maturity; uniform eight week photoperiodic flowering response to short days; peduncle length ranging from 8 to 15 cm on open, terminal sprays; medium plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora, and referred to by the cultivar name Tierno.*

Tierno, identified as 84-522002, was originated from a cross named by Cornelis P. VandenBerg in a controlled breeding program in Salinas, Calif., in 1984.

The female parent of Tierno was the cultivar identified as White Nova, disclosed in U.S. Plant Pat. No. 5,289. The male parent of Tierno was an unnamed seedling, identified as 78-@24002, having a daisy capitulum type, a nine week photoperiodic flowering response to short days, and medium plant height.

Tierno was discovered and selected as one flowering plant within the progeny of the stated cross by Cornelis P. VandenBerg on May 29, 1985, in a controlled environment in Salinas, Calif.

The first act of asexual reproduction of Tierno was accomplished when vegetative cuttings were taken from the initial selection in July of 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Tierno are firmly fixed and are retained through successive generations of asexual reproduction.

Tierno has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Tierno, which, in combination, distinguish this Chrysanthemum as a new and distinct cultivar:

1. Flat capitulum form.
2. Daisy capitulum type.

3. Red-purple ray floret color.
4. Diameter across face of capitulum up to 9 cm at maturity.
5. Uniform eight week photoperiodic flowering response to short days.
6. Peduncle length ranging from 8 to 15 cm on open terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Tierno, with the colors being as nearly true as possible with illustrations of this type.

Sheet 1 is a color photograph of Tierno grown as a single stem cut spray mum.

Sheet 2 is a black and white photograph of three views of the inflorescence of Tierno.

Sheet 3 is a black and white photograph showing the upper and under sides of the leaves of Tierno at three stages of development (mature, intermediate and immature).

Of the commercial cultivars known to the inventor, the most similar in comparison to Tierno is the unpatented but commercial cultivar Blue Marble. Reference is made to attached Chart A, which compares certain characteristics of Tierno to the same characteristics of Blue Marble.

Similar traits are capitulum form and type, diameter across face of capitulum and plant height. The ray floret color of Tierno is red-purple, while Blue Marble is lavender-pink. The spray formation of Tierno is always terminal, while the spray formation of Blue Marble is often compound. Tierno has shorter peduncles and a faster flowering response than Blue Marble. Under adverse conditions Blue Marble exhibits bract tissue in the disc. In trails of Tierno to date, the new cultivar has not shown bract tissue in the disc.

In the following description color references are made to The Royal Horticultural Society Colour Chart. The color values were determined on plant material grown in Salinas, Calif., on Apr. 28, 1989.

Classification:

*Botanical.*—*Dendranthema grandifora* cv Tierno.

*Commercial.*—Daisy cut spray mum.

INFLORESCENCE

A. Capitulum:

*Form.*—Flat.

*Type.*—Daisy.

*Diameter across face.*—Up to 9 cm at maturity.

B. Corolla of Ray Florets:

*Color (general tonality from a distance of three meters).*—Red-purple.

*Color (upper surface).*—Closest to 74D.

*Color (under surface).*—Closest to 70C to 70D.

*Shape.*—Straight, slightly ribbed and twisted.

C. Corolla of Disc Florets:

*Color (mature)*: Closest to 154B.

*Color (immature)*: Closest to 144B to 144C.

D. Reproductive Organ:

*Androecium.*—Present on disc florets only; no pollen.

*Gynoecium.*—Present on both ray and disc florets.

PLANT

A. General Appearance:

*Height.*—Medium; 90 to 100 cm as a single stem cut mum with two long day weeks prior to short days.

B. Foliage:

*Color (upper surface).*—147A.

*Color (under surface).*—147B.

*Shape.*—Lobed, slightly serrated.

CHART A

COMPARISON OF TIERNO AND BLUE MARBLE

| | TIERNO | BLUE MARBLE |
|---|---|---|
| Ray Floret Color | Red-purple | Lavender-pink |
| Capitulum Form and Type | Flat daisy | Flat daisy |
| Spray formation | Terminal | Terminal to compound |
| | 6 to 15 cm peduncles | 20 to 25 cm peduncles |
| Diameter Across Face of Capitulum | Up to 9 cm | Up to 9 cm |
| Plant Height | Medium | Medium |
| Flowering response period | 8 weeks | 9 weeks |

Comparisons Made of Plants Grown As Single Stem Spray Cut Mums In Salinas, California

I claim:

1. A new and distinct Chrysanthemum plant named Tierno, as described and illustrated.

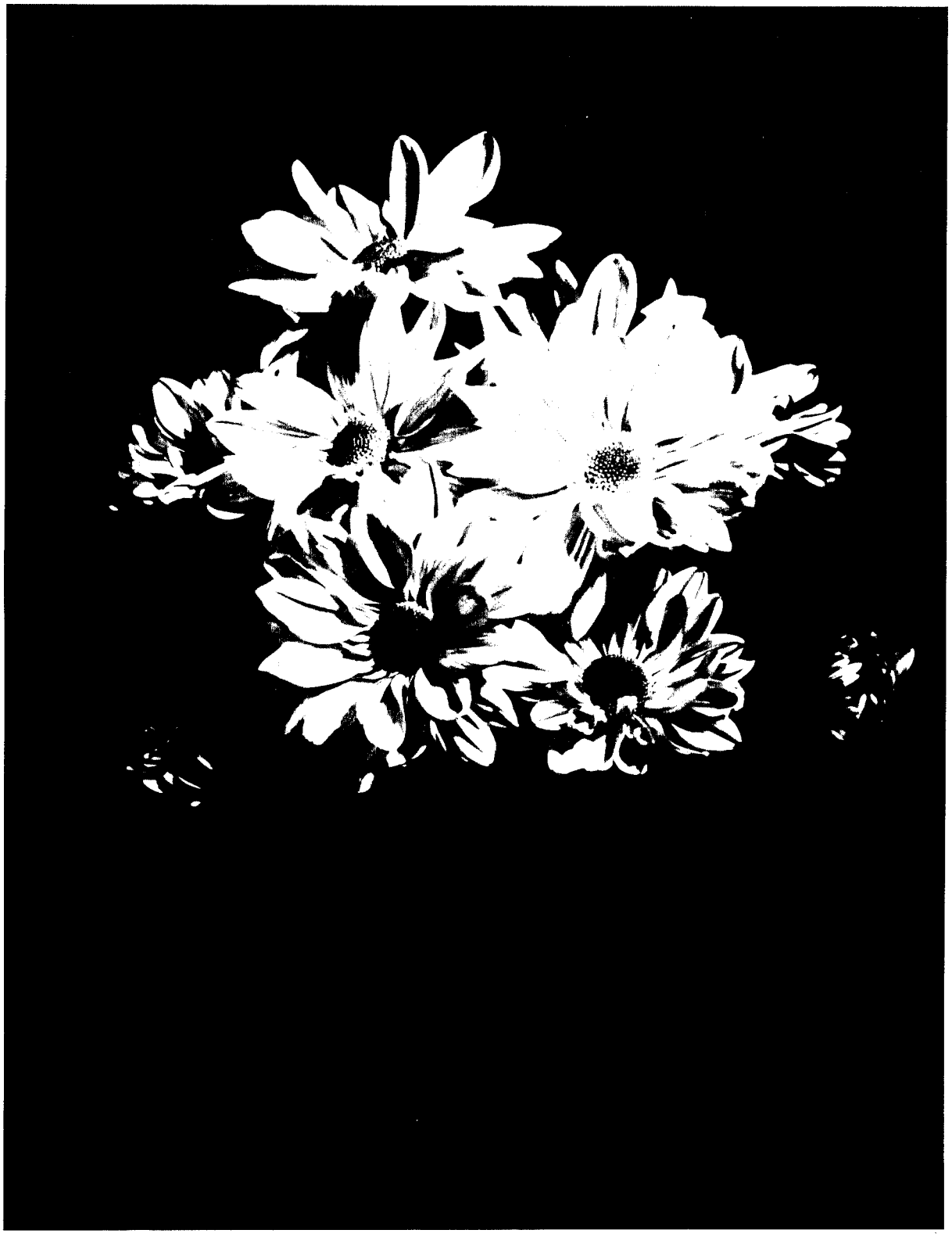

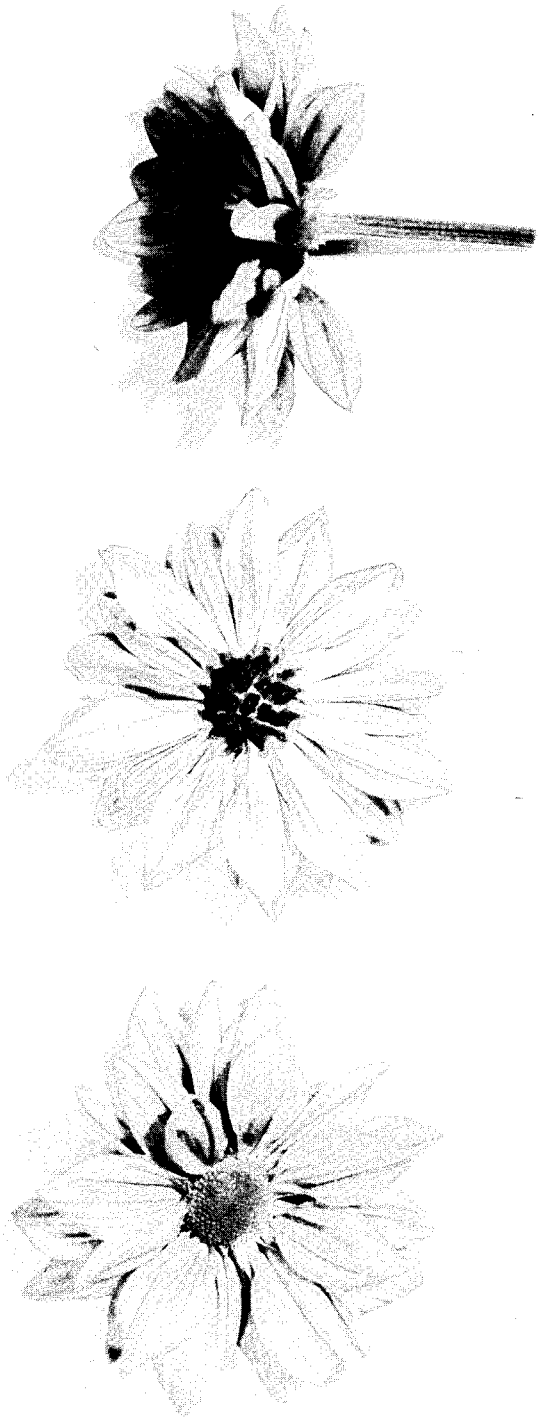

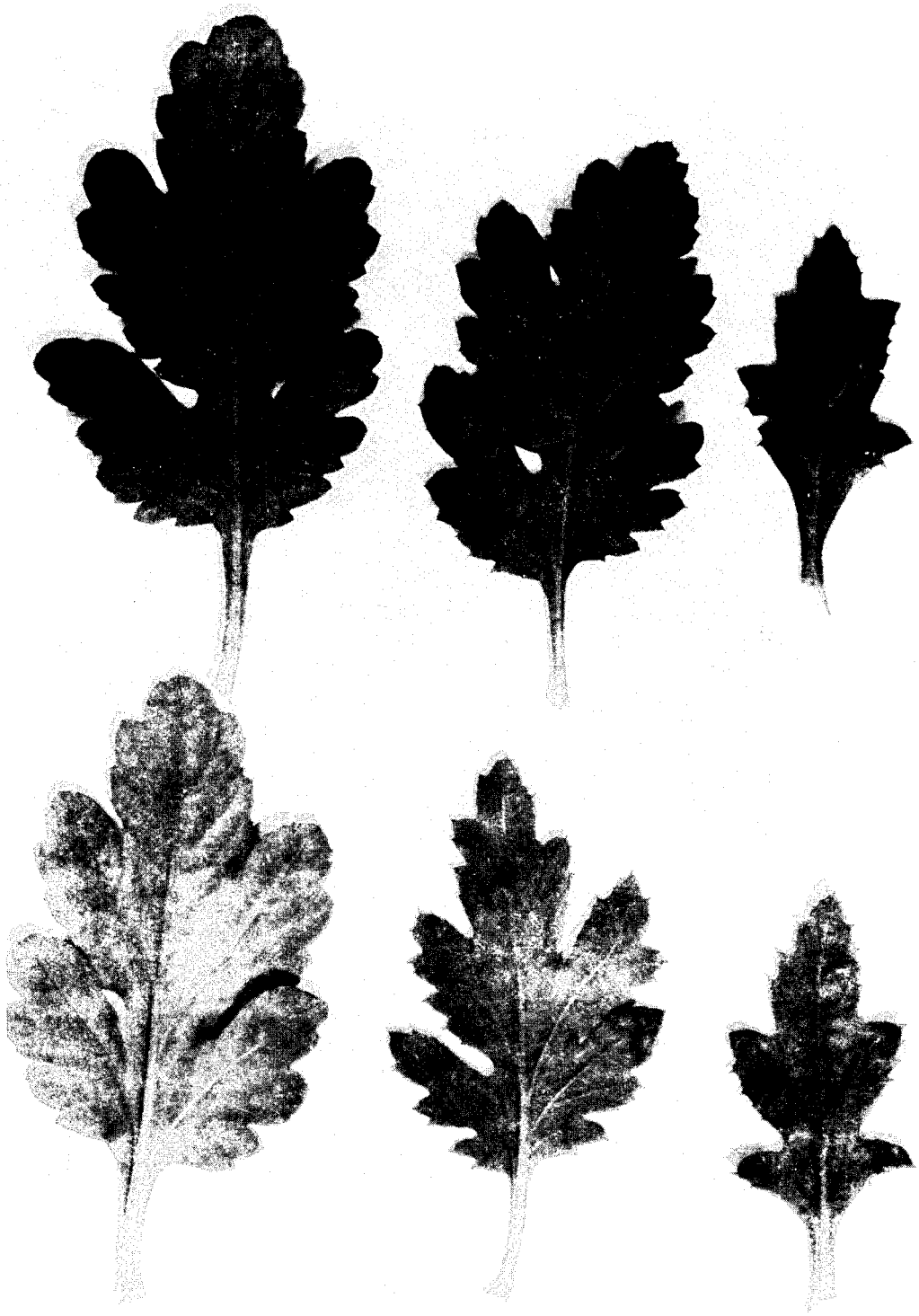

* * * * *